United States Patent [19]
Greenwood et al.

[11] Patent Number: 4,897,189
[45] Date of Patent: Jan. 30, 1990

[54] BLOOD PURIFICATION APPARATUS

[75] Inventors: Roger N. Greenwood; Colin Aldridge; James E. Tattershall, all of London; Rodney V. Barrett, Bristol, all of United Kingdom

[73] Assignee: Research Corporation Limited, London, England

[21] Appl. No.: 144,488

[22] Filed: Jan. 15, 1988

[30] Foreign Application Priority Data

Oct. 23, 1987 [GB] United Kingdom ................. 8724914

[51] Int. Cl.⁴ ...................... B01D 13/01; B01D 29/42
[52] U.S. Cl. ............................... 210/195.2; 210/257.2; 210/258; 210/321.72; 210/321.8; 210/321.88; 210/416.1; 422/45; 422/48; 604/5
[58] Field of Search ................. 422/45, 48, 44; 604/4, 604/5, 6; 210/195.2, 257.1, 257.2, 258, 321.72, 321.73, 321.74, 321.75, 321.76, 321.77, 321.78, 321.79, 321.8, 416.1, 321.82, 321.83, 321.84, 321.85, 321.86, 321.87, 321.88, 321.89

[56] References Cited

U.S. PATENT DOCUMENTS

| | | | |
|---|---|---|---|
| 4,331,540 | 5/1982 | Witsoe | 210/646 |
| 4,596,550 | 6/1986 | Troutner | 604/5 |
| 4,655,742 | 4/1987 | Vantard | 210/195.2 |

FOREIGN PATENT DOCUMENTS

| | | |
|---|---|---|
| 905407 | 3/1987 | Belgium . |
| 0114698 | 8/1984 | European Pat. Off. . |
| 0132210 | 1/1985 | European Pat. Off. . |

OTHER PUBLICATIONS

Robert R. Stromberg, "Development of a Novel Membrane Apheresis System for Plasma Collection at Mobile Sites", A.S.A.I.O. Transactions, vol. 33, No. 3.

Primary Examiner—W. Gary Jones
Attorney, Agent, or Firm—Scully, Scott, Murphy & Presser

[57] ABSTRACT

Blood purification apparatus comprises a dead-end system in which blood from the patient is allowed to flow through one or more purification modules, such as a dialyzer, a hemofilter, a hemoperfusion column and an oxygenator, into a resiliently walled reservoir, which is conveniently a standard blood bag. The direction of flow of the blood is then reversed by exertion of sufficient pressure on the bag to push the blood back through the purification module to the patient's circulation. Thus, since the reservoir is of available capacity, being of resilient material for example, the capacity of the apparatus remains equal to the volume of extra-corporeal blood.

13 Claims, 1 Drawing Sheet

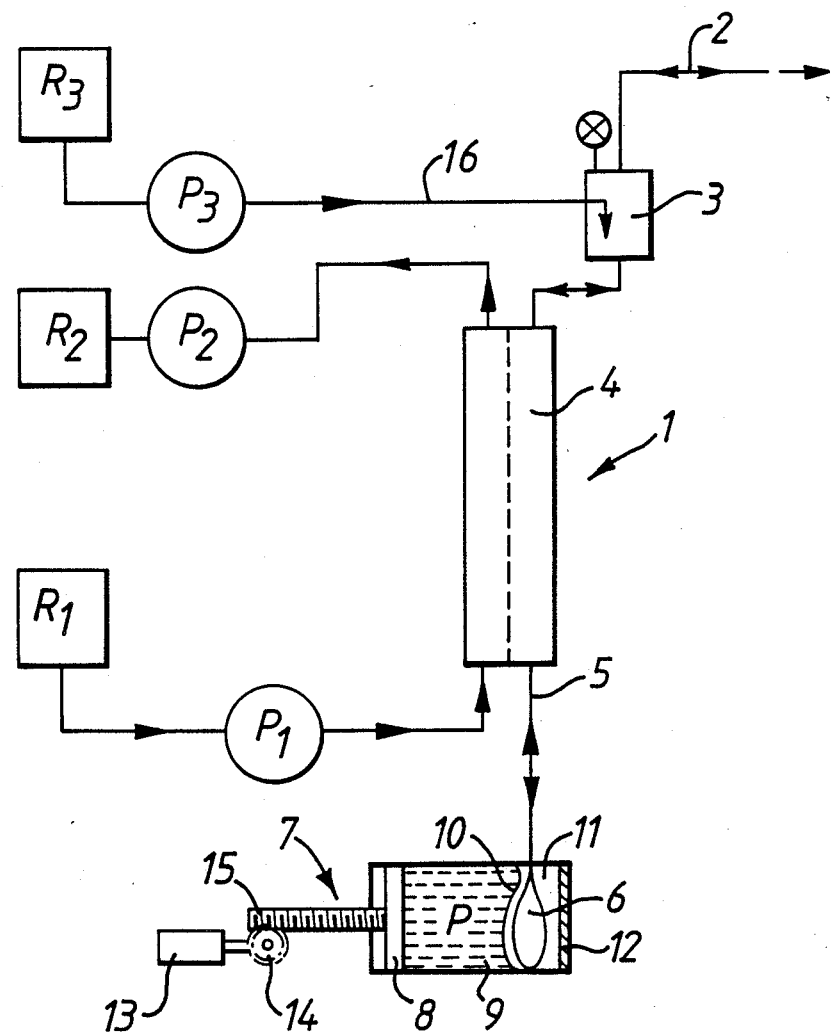

BLOOD PURIFICATION APPARATUS

BACKGROUND OF THE INVENTION

This invention relates to apparatus for the purification of blood, for example, by extracorporeal hemodialysis and/or hemofiltration and/or hemoperfusion. Hemodialysis is a widely used medical treatment for patients with acute and chronic renal failure. Hemofiltration is an alternative treatment gaining in popularity which involves massive removal of plasma water (approximately 30 liters) and replacement with sterile electrolyte solution. Hemoperfusion is a process for detoxifying blood of, for example, drug overdose, by contacting the blood with an adsorbent, such as activated carbon, to remove the toxins.

Hemodialysis services are normally supplied on an out-patient basis in specially constructed renal dialysis units or carried out at home by the patients themselves. Patients typically require three sessions of 4-6 hour duration per week. The hardware associated with hemodialysis tends to be provided as a fixed installation with the necessary plumbing and control apparatus.

Belgian Patent Number 905,407 (filed, 10th Sept. 1986, published 10th Mar. 1987) describes a single-needle hemodialysis system in which blood withdrawn by a pump from a patient suffering from renal insufficiency is passed through a dialyzer into an expansion chamber. The expansion chamber is in the form of a solid-walled, pressure resistant vessel having a line through which blood is delivered to and withdrawn from the vessel and also on air line extending from the vessel to a pressure sensor which has an associated control system operatively connected to the pump. As blood is delivered into the chamber by the pump the pressure of air, trapped in the vessel above the blood level, increases and is sensed by the sensor. When a preselected pressure is sensed by the pressure sensor, the control system sends a signal to the pumpp to reverse the direction of pumping thereby withdrawing the blood from the expansion chamber and returning it, via the dialyzer and pump, to the patient. Thereafter, when the sensed pessure falls to a preselected lower limit the control again reverses the direction of pumping to complete the cycle. A disadvantage of the proposed system is the danger inherent in the failure of the control which may result in dangerous, even fatal, amounts of air being introduced into the patient's circulation.

The most widely used hemodialysis system involves withdrawal of blood from the patient via a needle introduced into a vein supplied by a surgically created arteriovenous fistula, establishing a flow, using a peristaltic pump through a dialyzer with return to the patient's circulation via a second needle. Alternatively, a single needle is used in which case blood being taken from the fistula and returned to the fistula alternately by using twin pumps. A flow of dialysis fluid is established through the dialyzer across the remote side of the membrane from the blood and thence to drain. In order to achieve sufficient dialysis within an acceptable time frame, flow rates of both blood and dialysis fluid are high, typically from 200 ml/min to 400 ml/min for blood and 500 ml/min for dialysis fluid. The extra-corporeal blood volume of the dialysis system is high (300-450 ml) and large volumes of the dialysis fluid are required (120-160 liters per dialysis). The overall size of the installation and the complexity of the instrumentation is consequently great. It is these requirements along with the need for large volume of dialysis fluid which operate against portable units.

The foregoing description applies particularly to treatment of chronic renal failure. However, in acute renal failure which is a reversible condition which sometimes follows trauma, surgery or severe illness, patients may require blood purification during their stay in intensive care units. In this setting, a bulky dialysis machine and its associated parts and the need for special plumbing is, as best, inconvenient because of competition for space with other intensive care equipment such as respirators, drips and vital signs monitors. Also the complexities of operation of traditional dialysis machines cause problems for intensive care nursing staff who may not have been trained in renal units.

SUMMARY OF THE INVENTION

An object of the present invention is to obviate or mitigate the aforesaid disadvantages.

According to the present invention there is provided a blood purification apparatus comprising means for withdrawing blood from a patient into a blood conduit, a blood purification module in fluid flow communication with the conduit, a blood reservoir for receiving blood from the module and means for returning blood from the reservoir to the patient via the blood purification module. According to a preferred embodiment of the invention, blood purification apparatus comprises a blood conduit for receiving blood from a patient, a blood purification module in fluid flow communication with the conduit, a variable-capacity blood reservoir for receiving blood from the module and means for returning blood from the reservoir to the patient via the blood purification module so that the capacity of the apparatus is equal to and varies with the extracorporeal blood volume.

Preferably the blood purification module is a dialyzer, hemofilter, hemoperfusion unit or an oxygenator.

Preferably, the blood purification module is, or includes, a dialyzer and the apparatus includes means for passing dialysis fluid through the dialyzer. In a preferred embodiment, these means comprise a first reservoir for fresh dialysis fluid, a pump for passing fluid from the first reservoir to the dialyzer and a second reservoir for receiving and holding the entire effluent dialysis fluid from the dialyzer. It is preferred that the dialyzer be of the hollow fibre membrane type.

In a preferred embodiment of the invention, the means for withdrawing blood from and returning blood to the patient is a blood pump which may comprise a first chamber for hydraulic fluid, a second chamber separated from the first by a common flexible wall member, within the second chamber a flexible blood bag disposed proximate the flexible wall and in fluid flow communication with the blood purification module, and piston means within the first chamber disposed to act upon the hydraulic fluid. The piston is preferably motor driven, advantageously by a microprocessor controlled stepper motor.

The apparatus of the invention may also include means for injecting physiological fluid, such as an electrolyte solution, into the purified blood before return to the patient.

The invention will now be described, by way of example, with reference to the accompanying drawing which shows a flow diagram of the apparatus of the invention.

DETAILED DESCRIPTION OF THE PREFERRED EMBODIMENTS

Blood purification apparatus of the invention 1 has a blood conduit 2 for connection to a patient's blood supply via an intravenous needle or catheter (not shown). The conduit 2 conduits blood from the patient to a bubble trap 3 and hence to one side of the membrane of a dialyzer or hemofilter module 4. Blood line 5 conducts blood from the dialyzer module 4 to a blood bag 6.

Blood bag 6 is located within a pump assembly P, indicated generally as 7, which includes a piston 8 which acts upon hydraulic fluid in a first pump chamber 9 to distend or relax a flexible wall member 10. A second chamber 11 is formed by flexible wall member 10, in common with the first chamber, and rigid end closure plate 12. The blood bag is disposed in the second chamber between the plate 12 and the flexible wall member 10 so that when the piston 8 acts upon the hydraulic fluid in the first chamber 9, the flexible wall member 10 distends and exerts a sufficient squeezing action on the bag 6 to overcome the resistance of the blood circuit to return the blood to the patient. As piston 8 retracts blood is drawn from the patient.

The piston 8 may be motor driven by a motor 13 driving a worm gear 14 against a helically threaded piston shaft 15. It is convenient to use a stepper motor to facilitate microprocessor control of the speed and distance of travel of the piston and to monitor blood flow rates and volumes.

The apparatus 1 also includes reservoirs $R_1$ and $R_2$ for dialysis fluid and pump $P_1$ and $P_2$ for passing fluid from $R_1$ to $R_2$, via the dialyser module 4 on the remote side of the membrane from the blood. The receiving reservoir $R_2$ is of sufficient capacity to receive and hold the entire volume of dialysis fluid delivered from $R_1$ plus any additional water acquired in the dialyzer by ultra-filtration from the blood. This arrangement permits accurate measurement of fluid balance across the patient.

In use, blood is drawn from the patient into the blood bag 6 by the blood pump, flowing through the dialyzer module 4 wherein dialysis against dialysis fluid flowing across the remote side of the dialysis membrane occurs. Once a volume of blood has accumulated in the bag 6, then either immediately or after a time delay, the motor 13 is actuated for forward travel of the piston 8 to act via the hydraulic fluid in chamber 9 to distend the flexible wall 10 to press upon the bag 6 and reverse the direction of blood flow. Thus, the blood passes through the dialyser once in a forward direction and again in the reverse direction. It is believed that a certain time delay between forward and reverse cycles during which the blood is held stationary in the bag 6, may be advantageous to permit diffusion of solutes from the red blood cells through the cell wall into the plasma during this stationary period thus increasing the degree of dialysis during the reverse pass through the dialyzer.

In the intended application, that is in intensive care, the degree of treatment achieved on each pass need not be high as the treatment may be carried out continuously. Flow rates of blood and dialysis fluid may be comparatively low and the volume of dialysis fluid can be low. This gives the possibility of very gentle blood treatment and, as it is known that blood damage, leading to trauma, is a danger with extracorporeal treatments, this slow, gentle flow is a desirable feature of this invention. As a consequence of the low volumes of dialysis fluid which have to be handled, prepackaged sterile fluid packs may be used and the whole apparatus made self-contained in terms of its fluid requirements. Thus the apparatus may be portable and have small space requirements, making it eminently suitable for use in the equipment-crowded environment of an intensive care unit or as a part of the equipment carried on an ambulance.

The compact uncomplicated arrangement of the apparatus of the invention facilitates automatic control of the dialysis procedure. The blood pump 7 may be driven by a microprocessor controlled stepper motor from which, by counting the number and rate of revolution of the drive shaft using, for example, an optical interruption technique, the rate of treatment and volume of blood treated may be monitored. Should a residence time for the blood in the blood bag be desired this may easily be achieved by stopping the motor for the requisite time, under microprocessor control, before reversing its drive direction.

Using a pump at either end of the dialyzer allows the direction of flow of water across the membrane to be reversed in order to rehydrate the blood. It appears that reversal of the direction of flow of water across the dialyzer membrane may have a beneficial effect on the useful life of the dialyser. It is well known that during use the transport characteristics of dialysis membranes deteriorate with time because of fouling of the pores by large biomolecules such as proteins and lipids. There is strong evidence that reversal of the direction of ultrafiltration may dislodge some of the trapped fouling biomolecules thus reopening the pores and restoring the permeability of the membrane.

The invention has been described with reference to hemodialysis but it may alternatively or additionally be used in a hemoperfusion system. The dialysis module 4 may simply be removed and replaced by a carbon-packed hemoperfusion column, in which case the flow circuit for dialysis fluid is not required. Alternatively, a hemoperfusion column may be added to the dialysis circuit in serial fluid flow with the dialysis module. Similarly, as an alternative or addition to the dialyzer, a blood oxygenator may be used. Operating conditions for such alternative or additional units are well known in the art and are not particularly germane to the present invention.

During normal dialysis procedures a degree of removal of plasma water from the blood occurs, the mechanism involved being ultrafiltration. The ultrafiltration rate is controlled by the relative speeds of $P_1$ and $P_2$. In an alternative operating mode of the apparatus of the invention, the patient may be treated by a process known as hemofiltration. In this process plasma water is ultrafiltered from the blood under the action of $P_2$. Rehydration of the blood may be effected by introduction of a sterile replacement fluid from reservoir $R_3$ via pump $P_3$ and flow line 16 into the bubble trap 3 which is a convenient location for the introduction.

It will be understood that the apparatus of the invention may include such ancillarly equipment as is common in conventional dialysis machines for example, monitoring and control modules such as flow rate indicators and blood leak detectors. The apparatus would normally also include means for introducing anticoagulant, such as heparin, into the extracorporeal blood flow, as is usual in conventional dialysis procedures.

We claim:

1. Blood purification apparatus comprising means for withdrawing blood from a patient into a blood conduit, a blood purification module in fluid flow communication with said conduit, a blood reservoir for receiving blood from said module, pump means for withdrawing blood and returning blood from said reservoir to the patient via the blood purification module, said reservoir being flexible and having variable capacity and forming part of said pump means, the pump means comprising hydraulic fluid which can act on the exterior of said reservoir to control blood flow into and out of said blood purification module.

2. Apparatus as claimed in claim 1, wherein the blood purification module is a device selected from the group consisting of a dialyzer, a hemoperfusion unit, a hemofilter and an oxygenator.

3. Apparatus as claimed in claim 2, in which the blood purification module is a dialyzer of the hollow fibre membrane type.

4. Apparatus as claimed in claim 1, which includes a first reservoir for fresh dialysis fluid, pump means for passing fluid from the first reservoir to the blood purification module and a second reservoir for receiving and holding the entire effluent dialysis fluid or ultrafiltrate from the blood purification module.

5. Apparatus as claimed in claim 4, in which the pump means comprises a first pump intermediate the first reservoir and the blood purification module and a second pump intermediate the blood purification module and the second reservoir.

6. Apparatus as claimed in claim 5, in which the first and second pumps are of a type permitting selection of the direction of pumping.

7. Apparatus as claimed in claim 1, in which the pump means comprises a first chamber for hydraulic fluid, a second chamber separated from the first by a common flexible wall member, a flexible blood reservoir located within the second chamber proximate the flexible wall and in fluid flow communication with the blood purification module, and piston means within the first chamber disposed to act upon the hydraulic fluid.

8. Apparatus as claimed in claim 7, in which the piston is motor driven.

9. Apparatus as claimed in claim 8, in which the motor is a microprocessor controlled stepper motor.

10. Apparatus as claimed in claim 1, including means for introducing physiological fluid into the blood before return of the blood to the patient.

11. Apparatus as claimed in claim 1 comprising a dead-end system wherein the total blood volume of the apparatus is equal to and varies with the extracorporeal blood volume.

12. Apparatus as claimed in claim 1 in which the pump means includes a motor driven piston.

13. Apparatus as claimed in claim 12 in which the motor is a microprocessor controlled stepper motor.

* * * * *